United States Patent [19]

Dellaria et al.

[11] Patent Number: 5,426,111
[45] Date of Patent: Jun. 20, 1995

[54] [ALKOXY-, ALKENYLOXY-, ALKYNYLOXY-, AND PHENYLMETHYLOXYALKOXYCYCLOALKYL OR ALKOXYCYCLOHETEROALKYL]NAPHTHO[2,3-C]FURAN-1(3H)-ONE INHIBITORS OF 5-LIPOXYGENASE

[75] Inventors: Joseph F. Dellaria, Lindenhurst;
James D. Ratajczyk, Waukegan;
Clint D. W. Brooks, Libertyville;
Anwer Basha, Lake Forest, all of Ill.

[73] Assignee: Abbott Laboratories, Abbott Park, Ill.

[21] Appl. No.: 344,774

[22] Filed: Nov. 23, 1994

[51] Int. Cl.$^6$ .................. A61K 31/435; C07D 409/00; C07D 315/00; C07C 63/64
[52] U.S. Cl. .................. 514/277; 514/337; 514/438; 514/445; 514/449; 514/460; 514/473; 514/529; 549/60; 549/79; 549/299; 549/417; 549/476; 549/510; 546/269; 546/342; 562/467
[58] Field of Search .................. 549/60, 79, 299, 417, 549/476, 510; 546/269, 342; 562/467; 514/277, 337, 438, 445, 449, 460, 473, 529

Primary Examiner—C. Warren Ivy
Assistant Examiner—Amelia Owens
Attorney, Agent, or Firm—Jerry F. Janssen

[57] ABSTRACT

Compounds of formula

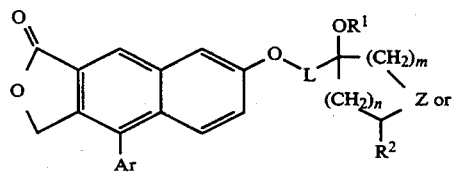

-continued

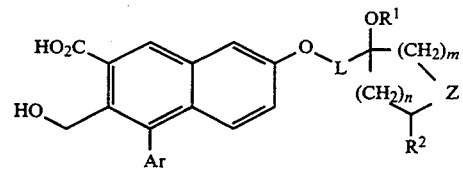

Ar is selected from (a) phenyl, (b) phenyl substituted with one or more groups selected from halogen, cyano, alkyl, haloalkyl, alkoxy, and alkoxycarbonyl, (c) furyl, (d) furyl substituted with one or more groups selected from halogen, alkyl, and alkoxy, (e) pyridyl, (f) pyridyl substituted with one or more groups selected from halogen, alkyl, and alkoxy, (g) thienyl, and (h) thienyl substituted with one or more groups selected from halogen, alkyl, and alkoxy; L is selected from alkylene of one to three carbon atoms, alkenylene of two to three carbon atoms, and alkynylene of two to three carbon atoms, and

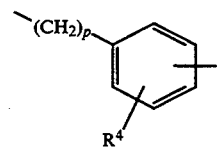

wherein p is an integer of 1 to 4, inclusive, and $R^4$ is selected from the group consisting of hydrogen, alkyl of one to four carbon atoms, halogen, haloalkyl of one to four carbon atoms, and alkoxy of one to six carbon atoms;

$R^1$ is alkyl; $R^2$ is hydrogen or alkyl; m is 1 or 2; Z is oxygen or CHOR$^3$, and n is 0 or 1 are potent inhibitors of lipoxygenase enzymes and thus inhibit the biosynthesis of leukotrienes. These compounds are useful in the treatment or amelioration of allergic and inflammatory disease states.

11 Claims, No Drawings

[ALKOXY-, ALKENYLOXY-, ALKYNYLOXY-, AND PHENYLMETHYLOXYALKOXYCYCLOALKYL OR ALKOXYCYCLOHETEROALKYL]NAPHTHO[2,3-C]FURAN-1(3H)-ONE INHIBITORS OF 5-LIPOXYGENASE

This invention relates to compounds having biological activity to inhibit lipoxygenase enzymes, to pharmaceutical compositions comprising these compounds, and to a medical method of treatment. More particularly, this invention concerns certain [alkyloxy-, alkenyloxy-, alkynyloxy-, and phenylmethyloxy-alkxoycycloalkyl or alkoxycycloheteroalkyl]naphtho[2,3-c]furan-1(3h)one and 3-hydroxymethyl-[alkyloxy-, alkenyloxy-, alkynyloxy-, and phenylmethyloxy-alkxoycycloalkyl or alkoxycycloheteroalkyl]-2-naphthoic acid compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis, cis-1,4-pentadiene structures, converting them to 1-hydroperoxy-trans, cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain [alkyloxy-, alkenyloxy-, alkynyloxy-, and phenylmethyloxy-alkxoycycloalkyl or alkoxycycloheteroalkyl]naphtho[2,3-c]furan- 1(3H)one and 3-hydroxymethyl-[alkyloxy-, alkenyloxy-, alkynyloxy-, and phenylmethyloxy-alkxoycycloalkyl or alkoxycycloheteroalkyl]-2-naphthoic acid compounds which inhibit lipoxygenase enzyme activity and are useful in the treatment of allergic and inflammatory disease states in which leukotrienes play a part.

The present invention provides a compound or a pharmaceutically acceptable salt thereof selected from the group consisting of

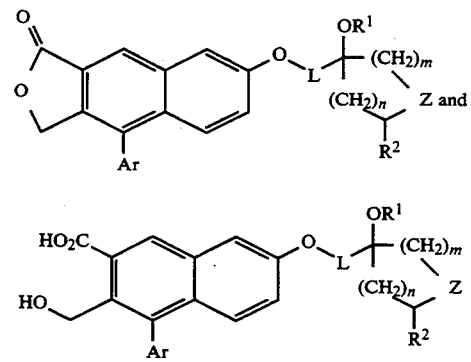

where Ar is selected from (a) phenyl, (b) phenyl substituted with one or more groups selected from halogen, cyano, alkyl of one to four carbon atoms, haloalkyl of one to four carbon atoms, alkoxy of one to six carbon atoms, and alkoxycarbonyl where the alkyl portion is of one to four carbon atoms, (c) furyl, (d) furyl substituted with one or more groups selected from halogen, alkyl of one to four carbon atoms, and alkoxy of one to four carbon atoms, (e) pyridyl, (f) pyridyl substituted with one or more groups selected from halogen, alkyl of one to four carbon atoms, and alkoxy of one to four carbon atoms, (g) thienyl, and (h) thienyl substituted with one or more groups selected from halogen, alkyl of one to four carbon atoms, and alkoxy of one to four carbon atoms.

L is selected from the group consisting of a) alkylene of one to three carbon atoms, b) alkenylene of two to three carbon atoms, c) alkynylene of two to three carbon atoms, and d)

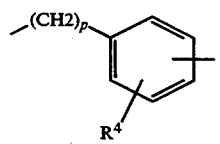

where p is an integer of 1 to 4 and $R^4$ is selected from the group consisting of hydrogen, alkyl of one to four carbon atoms, halogen, haloalkyl of one to four carbon atoms, and alkoxy of one to six carbon atoms.

$R^1$ is alkyl of one to four carbon atoms, alkenyl of two to four carbon atoms, alkynyl of two to four carbon atoms, or cyclopropylmethyl.

$R^2$ is hydrogen or alkyl of one to four carbon atoms, m is 1 or 2, Z is oxygen or >CHOR$^3$ wherein R$^3$ is alkyl of one to four carbon atoms, alkenyl of two to four carbon atoms, alkynyl of two to four carbon atoms, or cylcopropylmethyl, provided that when L is phenylalkyl or substituted phenylalkyl, Z is >CHOR$^3$, and n is 0 or 1.

In another embodiment, the present invention provides pharmaceutical compositions which comprise a therapeutically effective amount of compound as defined above in combination with a pharmaceutically acceptable carrier.

In yet another embodiment, the present invention provides a method of inhibiting leukotriene biosynthesis in a mammal in need of such treatment comprising administering to a mammal in need of such treatment a therapeutically effective amount of a compound as defined above.

DETAILED DESCRIPTION OF THE INVENTION

Definitions of Terms

The compounds of the invention may be administered in either the lactone or corresponding hydroxy acid form. The hydroxy acid compound is prepared from the lactone using methods well-known in the art such as treatment with aqueous base.

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)▽CH—, —CH$_2$CH=CHCH$_2$—, and the like.

The term "alkynylene" refers to a divalent group derived by the removal of two hydrogen atoms from a straight or branched chain acyclic hydrocarbon group containing a carbon-carbon triple bond. Examples of alkynylene include —CH$_2$CH≡,—CH≡CH—CH$_2$—, —CH≡CH—CH(CH$_3$)—, and the like.

The term "propynyl" refers to a straight chain, three-carbon group containing a carbon-carbon triple bond.

By "pharmaceutically acceptable salt" it is meant those salts which are, within the scope of sound medical judgement, suitable for use in contact with the tissues of humans and lower animals without undue toxicity, irritation, allergic response and the is like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Certain compounds of this invention may exist in either cis or trans or E or Z isomers with respect to the oxime geometry and in addition to stereoisomeric forms by virtue of the presence of one or more chiral centers. The present invention contemplates all such geometric and stereoisomers, including R- and S-enantiomers, diastereomers, and cis/trans or E/Z mixtures thereof as falling within the scope of the invention. If a particular enantiomer is desired, it may be prepared by asymmetric synthesis or by derivatization with a chiral auxiliary and the resulting diastereomeric mixture is separated and the auxiliary group cleaved to provide the pure desired enantiomers.

Preferred Embodiments

Compounds contemplated as falling within the scope of the invention include, but are not limited to 4-(4-fluorophenyl)-7-[3-(4-methoxytetrahydro-2H-pyran-4-yl)-2-propenyloxy]naptho [2,3-c]furan-1(3H)-one, 3-hydroxymethyl-4-(4-fluorophenyl)-7-[3-(4-methoxytetrahydro-2H-pyran-4-yl) -2-propenyloxy]-2-naphthoic acid, 4-(4-methoxyphenyl)-7-[3-(4-methoxytetrahydro-2H-pyran-4-yl)-2-propenyloxy]naptho [2,3-c]furan-1(3H)-one, 3-hydroxymethyl-4-(4-methoxyphenyl)-7-[3-(4-methoxytetrahydro-2H-pyran-4-yl) -2-propenyloxy]-2-naphthoic acid, 4-(2-fluorophenyl)-7-[3-(4-methoxytetrahydro-2H-pyran-4-yl)-2-propenyloxy]naptho [2,3-c]furan-1(3H)-one, 3-hydroxymethyl-4-(2-fluorophenyl)-7-[3-(4-methoxytetrahydro-2H-pyran-4-yl)-2-propenyloxy]-2-naphthoic acid, 4-(fur-2-yl)-7-[3-(4-methoxytetrahydro-2H-pyran-4-yl)-2-propenyloxy]naptho [2,3-c]furan-1(3H)-one, 3-hydroxymethyl-4-(fur-2-yl)-7-[3-(4-methoxytetrahydro-2H-pyran-4-yl)-2-propenyloxy]-2-naphthoic acid, 4-(fur-3-yl)-7-[3-(4- methoxytetrahydro-2H-pyran-4-yl)-2-propenyloxy]naptho [2,3-c]furan-1(3H)-one, 3-hydroxymethyl-4-(fur-3-yl)-7-[3-(4-methoxytetrahydro-2H-pyran-4-yl) -2-propenyloxy]-2-naphthoic acid, 4-(thien-3-yl)-7-[3-(4- methoxytetrahydro-2H-pyran-4-yl)-2-propenyloxy]naptho [2,3-c]furan-1(3H)-one, 3-hydroxymethyl-4-(thien-3-yl)-7-[3-(4-methoxytetrahydro-2H-pyran-4-yl) -2-propenyloxy]-2-naphthoic acid, 4-(4-fluorophenyl)-7-[3-(4-methoxytetrahydro-2H-pyran-4-yl)-2propynylox]naptho [2,3-c ]furan-1(3H)-one, 3-hydroxymethyl-4-(4-fluorophenyl)-7-[3-(4-methoxytetrahydro-2H-pyran-4- yl) -2propynyloxy]-2-napthoic acid, 4-(4-fluorophenyl)-7-[3-(4-methoxytetrahydro-2H-pyran-4-yl)propyloxy]naptho [2,3-c]furan-1(3H)-one, 3hydroxymethyl-4-(4-fluorophenyl)-7-[3-(4-methoxytetrahydro-2H-pyran-4-yl)propyloxy]-2-napthoic acid, 4-(4-fluorophenyl)-7-[3-(2-methyl-4-methoxytetrahydro-2H-pyran4-yl)-2-propenyloxy]naptho[2,3-c]furan-1(3H)-one, 3-hydroxymethyl-4-(4-fluorophenyl)-7-[3-(2-methyl-4-methoxytetrahydro-2H-pyran-4-yl)-2-propenyloxy]-2-napthoic acid, 4-(fur-2-yl)-7-[3-(2-methyl-4-methoxytetrahydro-2H-pyran-4-yl)-2-propenyloxy]naptho[2,3-c]furan-1(3H) -one, 3-hydroxymethyl-4-(fur-2-yl)-7-[3-(2-methyl-4-methoxytetrahydro-2H-pyran-4-yl) -2-propenyloxy]-2-napthoic acid, 4-(fur-3-yl)-7-[3-(2-methyl-4-methoxytetrahydro-2H-pyran-4-yl)-2-propenyloxy]naptho[2,3-c]furan-1(3H)-one, 3-hydroxymethyl-4-(fur-3-yl)-7-[3-(2-methyl-4-methoxytetrahydro-2H-pyran-4-yl) -2-propenyloxy]-2-napthoic acid, 4-(thien-3-yl)-7-[3-(2-methyl-4-methoxytetrahydro-2H-pyran-4-yl)-2-propenyloxy]naptho[2,3-c]furan-1(3H)-one, 3-hydroxymethyl-4-(thien-3-yl)-7-[3-(2-methyl-4-methoxytetrahydro-2H-pyran-4-yl) -2-propenyloxy]-2-napthoic acid, 4-(4-fluorophenyl)-7-[[3-(trans-1,4-dimethoxycyclohexyl)phenyl]methoxy]naptho[2,3-c]furan -1(3H)-one, 3-hydroxymethyl-4-(4-fluorophenyl)-7-[[3-(trans-1,4-dimethoxycyclohexyl)phenyl]methoxy]-2napthoic acid, 4-(fur-2-yl)-7-[[3-(trans-1,4-dimethoxycyclohexyl)phenyl]methoxy]naptho[2,3-c]furan-1(3H)-one, 3-hydroxymethyl-4-(fur-2-yl)-7-[[3-(trans-1,4-dimethoxycyclohexyl)phenyl]methoxy]-2-napthoic acid, 4-(fur-3-yl)-7-[[3-(trans-1,4-dimethoxycyclohexyl)phenyl]methoxy]naptho[2,3-c]furan-1(3H)-one, 4-(fur-3-yl)-7-[[3-(trans-1,4-dimethoxycyclohexyl)phenyl]methoxy]-2-napthoic acid, 4-(thien-3-yl)-7-[[3-(trans-1,4-dimethoxycyclohexyl)phenyl]methoxy]naptho-[2,3-c]furan -1(3H)-one, 4-(thien-3-yl)-7-[[3-(trans-1,4-dimethoxycyclohexyl)phenyl]methoxy]-2-napthoic acid, 4-(4-fluorophenyl)-7-[[3-(trans-1,3-dimethoxycyclobutyl)phenyl]methoxy]naptho-[2,3-c]furan -1(3H)-one, 3-hydroxymethyl-4-(4-fluorophenyl)-7-[[3-(trans-1,3-dimethoxycyclobutyl)phenyl]methoxy]-2-napthoic acid, 4-(fur-2-yl)-7-[[3-(trans-1,3-dimethoxycyclobutyl)phenyl]methoxy]naptho-[2,3-c]furan -1(3H)-one, 3-hydroxymethyl-4-(fur-2-yl)-7-[[3-(trans-1,3-dimethoxycyclobutyl)phenyl]methoxy]-2-napthoic acid, 4-(fur-3-yl)-7-[[3-(trans-1,3-dimethoxycyclobutyl)phenyl]methoxy]naptho[2,3-c]furan-1(3H)-one, 3-hydroxymethyl-4-(fur-3-yl)-7-[[3-(trans-1,3-dimethoxycyclobutyl)phenyl]methoxy]-2-napthoic acid, 4-(thien-3-yl)-7-[[3-(trans-1,3-dimethoxycyclobutyl)phenyl]methoxy]naptho-[2,3-c]furan -1(3H)-one, and 3-hydroxymethyl-4-(thien-3-yl)-7-[[3-(trans-1,3-dimethoxycyclobutyl)phenyl]methoxy]-2-napthoic acid, or a pharmaceutically acceptable salt thereof.

In one preferred embodiment, the present invention provides compounds of the formula

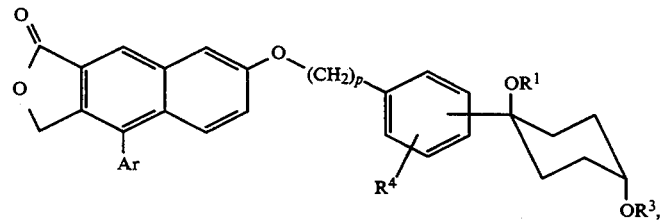

or the corresponding ring-opened hydroxy acid form thereof, wherein p is of one to four carbon atoms and $R^4$ is selected from the group consisting of alkyl of one to four carbon atoms, halogen, haloalkyl of one to four carbon atoms, or alkoxy of one to six carbon atoms; $R^1$ and $R^3$ are alkyl of one to four carbon atoms; and Ar is defined above.

In another preferred embodiment, compounds of the present invention are of the formula

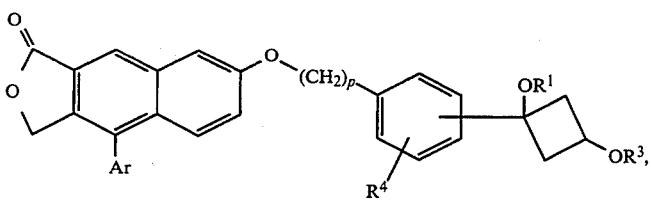

or the corresponding hydroxy acid form thereof, wherein p, Ar, $R^1$, $R^2$, and $R^4$ are as defined immediately above.

In yet another preferred embodiment, compounds of the present invention have the formula,

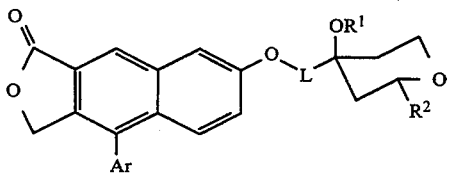

or the corresponding hydroxy acid form thereof, where L is alkylene of one to three carbon atoms, alkenylene of two to three carbon atoms, or alkynylene of two to three carbon atoms, and Ar, $R^1$ and $R^2$ are defined above.

The most preferred compounds of the invention have the structure immediately above, or the corresponding hydroxy acid form thereof, where Ar is unsubstituted phenylalkyl or phenylalkyl substituted with halogen, cyano, alkyl of one to four carbon atoms, haloalkyl of one to four carbon atoms, alkoxy of one to six carbon atoms, and alkoxycarbonyl where the alkyl portion is of one to four carbon atoms, and $R^1$, $R^2$, and L are defined immediately above.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23 187 challenge (final concentration of 8.3 µM) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis in human whole blood. A representative result for a particular example is 55% inhibition @ 100 nm for 4-(4-fluorophenyl)-7-[(3'-(4"-methoxytetrahydropyran-4"-yl)prop-2'-eneyloxy)]naptho[2,3-c]furan-1(3H)-one (Example 1).

Pharmaceutical Compositions

The present invention also provides pharmaceutical compositions which comprise compounds of the present invention formulated together with one or more non-toxic pharmaceutically acceptable careers. The pharmaceutical compositions may be specially formulated for oral administration in solid or liquid form, for parenteral injection, or for rectal administration.

The pharmaceutical compositions of this invention can be administered to is humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium as chloride, and the like. Prolonged absorption of the injectable pharmaceutical form may be brought about by the inclusion of agents which delay absorption such as aluminum monostearate and gelatin.

In some cases, in order to prolong the effect of the drag, it is desirable to slow the absorption of the drag from subcutaneous or intramuscular injection. This may be accomplished by the use of a liquid suspension of crystalline or amorphous material with poor water solubility. The rate of absorption of the drag then depends upon its rate of dissolution which, in turn, may depend upon crystal size and crystalline form. Alternatively, delayed absorption of a parenterally administered drug form is accomplished by dissolving or suspending the drag in an oil vehicle.

Injectable depot forms are made by forming microencapsule matrices of the drag in biodegradable polymers such as polylactide-polyglycolide. Depending upon the ratio of drag to polymer and the nature of the particular polymer employed, the rate of drag release can be controlled. Examples of other biodegradable polymers include poly(orthoesters) and poly(anhydrides) Depot injectable formulations are also prepared by entrapping the drag in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the is active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of the Invention

The compounds of this invention are obtained by a variety of synthetic routes. Representative procedures are outlined as follows. It should be understood that the groups $R^1$, $R^2$, and Z, as used herein, correspond to the groups identified above.

The preparation of compounds in which L is alkylene, alkenylene, or alkynylene is shown is Scheme 1. Tertiary alcohol 3 is prepared by condensation of the magnesium salt of O-THP propargyl alcohol and cyclic ketone 2. Alkylation of 3 by treatment with base, preferably NaH and $R^1X$ where X is a suitable leaving group such as bromo, chloro, iodo, methanesulfonyl, trifluoromethanesulfonyl, or p-toluenesulfonyl provides 4. The THP protecting group is then removed, preferably using pyridinium p-toluenesulfonate in methanol, and the resulting primary alcohol 5 is convened to iodide 6, preferably by conversion to the methanesulfonyl derivative with methanesulfonyl chloride, followed by treatment with NaI to form the iodide. Iodide 6 is coupled with lactone 7, preferably using $K_2CO_3$ in DMF, to form alkynyl derivative 8. Lactones 7 are prepared as described in U.S. Pat. Nos. 5,227,399 and 5,252,599.

Alkenyl derivatives 10 are prepared by selective reduction of alkynol 5 to the trans olefin, preferably using RED-AL (sodium bis(2-methoxyethoxy)aluminum hydride, Aldrich Chemical Co.), followed by conversion to the iodide and coupling with 7 as described above.

Saturated derivative 12 is prepared by reduction of olefin 9, preferably by catalytic hydrogenolysis using palladium on calcium carbonate poisoned with lead to form 11, followed by conversion to the iodide and coupling with 7 as described above.

hol 16, which is converted to representative compound 17 by coupling with lactone 7 under standard Mitsunobu conditions (triphenylphosphine, diethyl or diisopropylazodicarboxylate; see Mitsunobu, O., *Synthesis*, 1981, 1).

Scheme 2

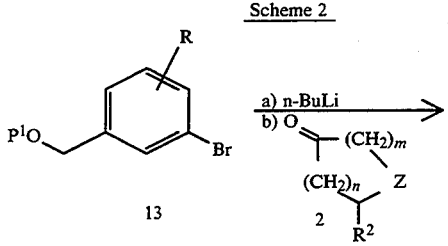

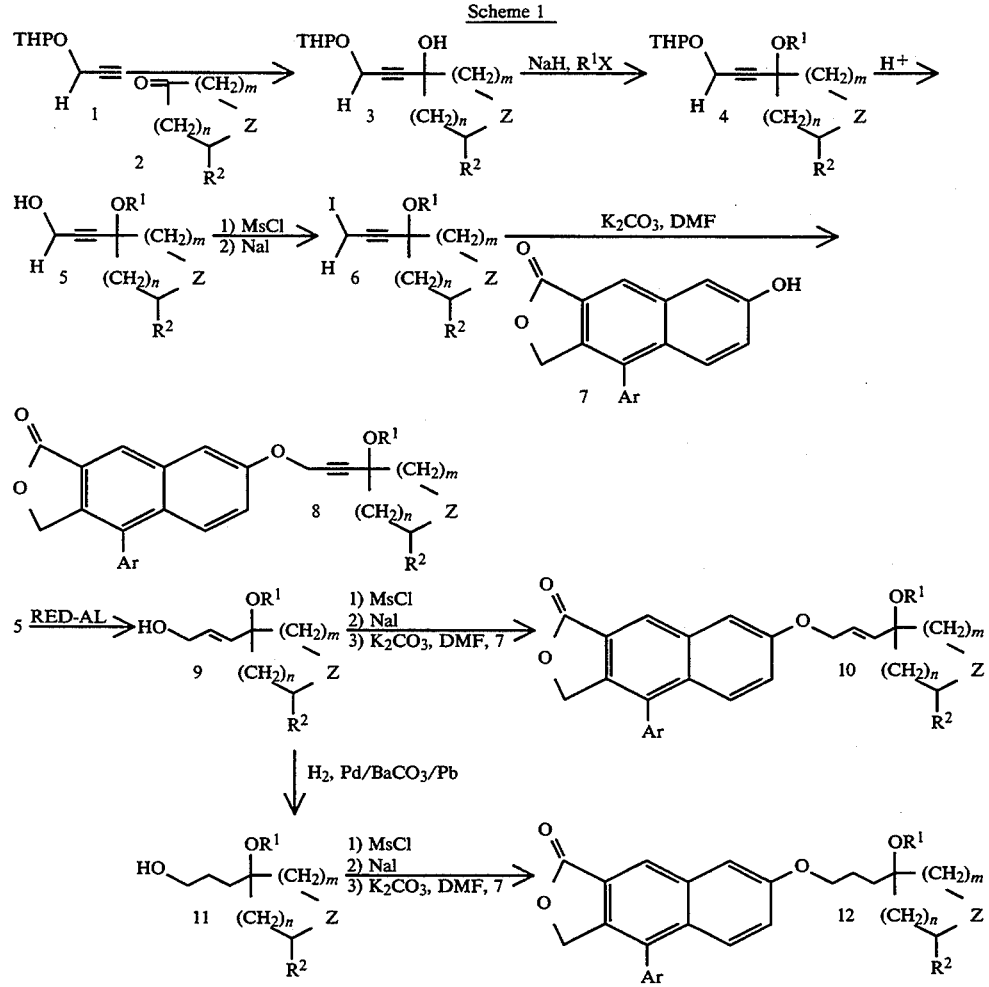

The preparation of compounds in which L is substituted or unsubstituted phenyl is outlined in Scheme 2. The starting bromobenzyl alcohol is protected with a suitable protecting group $P^1$ to form 13 where R is hydrogen, alkyl, haloalkyl, or alkoxy. Suitable protecting groups may be found in Greene, Protective Groups in Organic Synthesis, [date, publisher, etc.]. A preferred protecting group is allyloxy. Protected alcohol 13 is then metallated using, for example, n-butyllithium in an organic solvent such as THF. Addition of ketone 2 provides alcohol 14, which is alkylated as described above to form 15. Removal of $P^1$ provides benzyl alco-

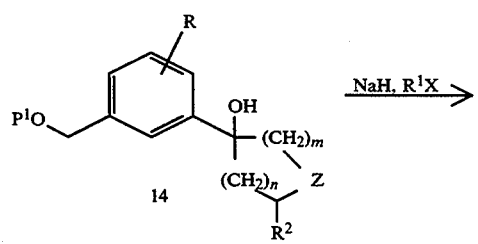

-continued
Scheme 2

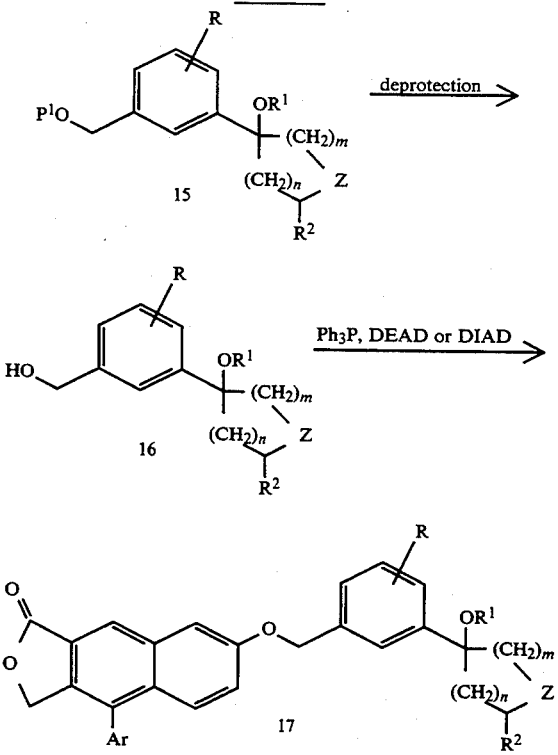

The foregoing may be better understood by the following examples which are presented for purposes of illustration and are not intended to limit the scope of the invention.

EXAMPLE 1

Preparation of 4-(4-fluorophenyl)-7-[3-(4-methoxytetrahydro-2H-pyran-4-yl)-2-propenyloxy]napth]naptho[2,3-c]furan-1(3H)-one.

Step 1:
4-hydroxy-4-[3-(tetrahydropyran-2-yloxy)prop-1-ynyl]-tetrahydropyran.

Tetrahydro-2-(2-propynyloxy)-2H-pyran (21 g, 150 mmol) was converted to the corresponding magnesium anion by deprotonation with ethyl magnesium bromide (75 mL of a 2M solution, 150 mmol) according to the method described in Org. Synth., 60: 81, 7 (1981). The resulting anion was cooled to −20° C. and tetrahydro-4H-pyran-4-one (14.8 g, 148 mmol) in dry THF (30 mL) was added dropwise and the resulting solution stirred for three hours. The reaction was quenched by addition of crushed ice and saturated aqueous NH$_4$Cl. The resulting two-layered mixture was extracted with ether (3×150 mL). The combined organic layers were dried over MgSO$_4$, filtered, and concentrated in vacuo. Purification by chromatography on silica gel (200 g, 20% ethyl acetate: hexanes) provided 4-hydroxy-4-[3-(tetrahydropyran-2-yloxy)prop-1-ynyl]tetrahydropyran(31.4 g, 88%).

Step 2:
4-methoxy-4-[3-(tetrahydropyran-2-yloxy)prop-1-ynyl]tetrahydropyran.

To a suspension of sodium hydride (1.2 g of an 80% oil dispersion, 50 mmol) in dry THF (45 mL) was added a solution of 4-hydroxy-4-[3-(tetrahydropyran-2-yloxy)-prop-1-ynyl]tetrahydropyran(3.71 g, 15.3 mmol), prepared as in step 1. After hydrogen evolution ceased, methyl iodide (3.0 mL, 48.2 mmol) was added neat and the resulting solution was stirred overnight at ambient temperature. The reaction was quenched by addition of crushed ice and saturated aqueous NH$_4$Cl. The resulting two-phase mixture was extracted with ether (3×100 mL). The combined organic layers were dried over MgSO$_4$, filtered, and concentrated in vacuo. Purification by chromatography on silica gel (100 g, 10% ethyl acetate: hexanes) provided 4-methoxy-4-[3-(tetrahydropyran-2-yloxy)prop-1-ynyl]tetrahydropyran (3.74 g, 95 %) as a colorless oil.

Step 3:
4-methoxy-4-(3-hydroxyprop-1-ynyl)tetrahydropyran.

To a solution of 4-methoxy-4-[3-(tetrahydropyran-2-yloxy)-prop-1-ynyl]tetrahydropyran (3.8 g, 14.8 mmol), prepared as in step 2, in methanol (50 mL), was added a catalytic amount of pyridinium p-toluenesulfonate (PPTS). The resulting yellow solution was stirred under nitrogen for 17 hours at ambient temperature. The volatiles were removed in vacuo and the residue was dissolved in ethyl acetate and treated with saturated aqueous NH$_4$Cl. The organic layer was dried over MgSO$_4$, filtered, and concentrated in vacuo. Purification by chromatography on silica gel (100 g, 30% ethyl acetate: hexanes) provided 4-methoxy-4-(3-hydroxy-prop-1-ynyl)tetrahydropyran (1.2 g, 47 %) as a colorless oil.

Step 4:
4-methoxy-4-(3-hydroxy-trans-prop-1-enyl)tetrahydropyran.

A solution of 4-methoxy-4-(3-hydroxyprop-1-ynyl)-tetrahydropyran (10.8 g, 44.9 mmol), prepared as in step 3, in dry THF (100 mL) was cooled to −75° C., and RED-AL (sodium bis(2-methoxyethoxy)aluminum hydride, Aldrich Chemical Co., 20 mL of 3.4M solution in toluene, 68 mmol) was added under a dry argon atmosphere. The cooling bath was removed and the reaction was warmed to 0° C. and quenched by addition of crushed ice and saturated aqueous NH$_4$Cl. The resulting two-phase mixture was extracted with ethyl acetate (4×90 mL). The combined organic layers were dried over MgSO$_4$, filtered, and concentrated in vacuo. Purification by chromatography on silica gel (100 g, 10% ethyl acetate: hexanes) provided 4-methoxy-4-(3-hydroxy -trans-prop-1-enyl)tetrahydropyran(3.71 g, 34 %) as a colorless oil.

Step 5.
4-methoxy-4-(3-methanesulfonyl-trans-prop-1-enyl)tetrahydropyran.

4-methoxy-4-(3-hydroxy-trans-prop-1-enyl)tetrahydropyran, prepared as in step 4, was convened to the corresponding mesylate according to the method of Crossland and Servis, J. Org. Chem., 35, 3195–3196 (1970).

Step 6. Preparation of 4-methoxy-4-(3-iodo-trans-prop-1-enyl)tetrahydropyran.

To a 0° C. solution in acetone of 4-methoxy-4-(3-methanesulfonyl-trans-prop-2-enyl)tetrahydropyran (505 mg, 2.02 mmol), prepared as in step 5 was added sodium iodide (605 mg, 4.03 mmol), and the reaction was stirred for 15 min. The reaction was partitioned between ethyl acetate and brine. The organic layer was washed twice with brine, dried over MgSO4, filtered and concentrated in vacuo to provide 4-methoxy-4-(3-iodo-trans-propenyl)tetrahydropyran (550 mg, 97%) as a dark yellow oil. The iodide was of sufficient purity to use without further purification.

Step 7:
4-(4-fluorophenyl)-7-[3-(4-methoxytetrahydro-2H-pyran-4-yl)-2-propenyloxy]naptho[2,3-c]furan-1(3H)-one.

A solution of 7-hydroxy-4-(4-fluorophenyl) naptho[2,3-c]furan-1(3H)-one (303 mg, 1.03 mmol), prepared as described in U.S. Pat. No. 5,227,399, 4-(3-iodo-trans-prop-1-enyl)-4-methoxytetrahydropyran (480 mg, 1.70 mmol), prepared as in step 6, and finely ground anhydrous K2CO3 (365 mg, 2.64 mmol) in dry DMF (10 mL) was heated at 55° C. for 2 hours and then cooled to ambient temperature and partitioned between water and ethyl acetate. The organic layer was washed once with aqueous 1N NaOH and twice with brine, dried over MgSO4, filtered, and concentrated in vacuo to provide a tan solid (0.54 g). Purification by flash chromatography (silica gel, 0.5L 30% ethyl acetate:hexanes, then 0.5L 40% ethyl acetate: hexanes) provided 4,-(4-fluorophenyl)-7-[3-(4-methoxytetrahydro-2H-pyran-4-yl)-2-propenyloxy]naptho[2,3-c]furan-1(3H)-one (234 mg) as a solid. Recrystallization from ether/hexanes provided analytically pure compound (197 mg, 43%). mp 144°–148° C. $^1$H NMR (300 MHz, CDCl3) δ8.38 (1H, s), 7.66 (1H, d, J=9.5 Hz),7.22-7.49 (6H, m), 5.91 (1H, dr, J=15.5, 4.5 Hz), 5.82 (1H, d, J=15.5 Hz), 5.23 (2H, s), 4.76 (2H, d, J=4.5 Hz), 3.68-3.82 (4H, m), 3.27 (3H, s), 1.75-1.82 (4H, m). MS m/e 466 (M+NH4)+. Analysis calc'd for $C_{27}H_{25}O_5F$: C, 72.31; H, 5.62. Found: C, 72.24; H, 5.52.

EXAMPLE 2

Preparation of 4-(4-fluorophenyl)-7-[3-(4-methoxytetrahydro-2H-pyran-4-yl)-2-propynyloxy]naptho[2,3-c]furan-1(3H)-one.

The desired compound is prepared according to the method of Example 1, steps 1-3 and 5-7.

EXAMPLE 3

Preparation of 4-(4-fluorophenyl)-7-[3-(4-methoxytetrahydro-2H-pyran-4-yl)propyloxy]naptho[2,3-c]furan-1(3H)-one.

Step 1:
4-methoxy-4-(3-hydroxypropyl)tetrahydropyran.

The desired compound is prepared by catalytic hydrogenolysis of 4-methoxy-4-(3-hydroxy-trans-prop-1-enyl) tetrahydropyran, prepared as in Example 1, steps 1-4, using palladium on calcium carbonate poisoned with lead according to the method of U.S. Pat. No. 5,268,379, Example 5.

Step 2:
4-(4-fluorophenyl)-7-[3-(4-methoxytetrahydro-2H-pyran-4yl)propyloxy]napho [2,3-c]furan-1(3H)-one.

The desired compound is prepared according to the method of Example 1, steps 5-7, except substituting 4-methoxy-4-(3-hydroxypropyl)tetrahydropyran, prepared as in step 1, for 4-methoxy-4-(3-hydroxy-trans-propenyl)tetrahydropyran.

EXAMPLE 4

Preparation of 4-(4-fluorophenyl)-7-[3-(2-methyl-4-methoxytetrahydro-2H-pyran-4-yl) -2-propenyloxy)]naptho[2,3-c]furan-1(3H)-one.

The desired compound is prepared according to the method of Example 1, except substituting 2-methyltetrahydro-4H-pyran-4-one for tetrahydro-4H-pyran-4one in step 1.

The compounds listed in Table 1 are prepared according to the method of Example 1 (R=H), or Example 4 (R=CH3), except substituting the desired 7-hydroxy-4-(aryl)naptho [2,3-c]furan-1(3H)-one, prepared as described in U.S. Pat. No. 5, 227,399, or 7-hydroxy-4-(heteroaryl)naptho[2,3-c]furan-1(3H)-one, prepared as described in U.S. Pat. No. 5,252,599 for 7-hydroxy-4-(4fluorophenyl)naptho[2,3-c]furan-1(3H)-one.

TABLE 1

| Example | R² | Ar |
|---------|-----|-----|
| 5 | H | phenyl |
| 6 | CH3 | phenyl |
| 7 | H | 4-chlorophenyl |
| 8 | CH3 | 4-chlorophenyl |
| 9 | H | 4-methoxyphenyl |
| 10 | CH3 | 4-methoxyphenyl |
| 11 | H | 2-chlorophenyl |
| 12 | CH3 | 2-chlorophenyl |
| 13 | H | 2-fluorophenyl |
| 14 | CH3 | 2-fluorophenyl |
| 15 | H | 3-methoxyphenyl |
| 16 | CH3 | 3-methoxyphenyl |
| 17 | H | 2-furyl |
| 18 | CH3 | 2-furyl |
| 19 | H | 3-furyl |
| 20 | CH3 | 3-furyl |
| 21 | H | 3-thienyl |
| 22 | CH3 | 3-thienyl |
| 23 | H | 3-pyridyl |
| 24 | CH3 | 3-pyridyl |

EXAMPLE 25

Preparation of 4-(4-fluorophenyl)-7-[[3'-(trans-1,4-dimethoxycyclohexyl)phenyl]methoxy]naptho[2,3-c]furan-1(3H)-one.

Step 1: 3-allyloxymethylbromobenzene.

The desired compound is prepared by reaction of 3-bromobenzyl alcohol with NaH and allyl bromide.

Step 2.
4-hydroxy-4-[3-allyloxymethylphenyl]cyclohexan-1-one ethylene glycol ketal.

The desired compound is prepared by metallation of 3-allyloxymethylbromobenzene, prepared as in step 1, with n-butyllithium at −78° C., followed by condensation with 1,4-cycloheaxanedione mono-ethylene glycol ketal.

Step 3.
4-methoxy-4-[3-allyloxymethylphenyl]cyclohexan-1-one ethylene glycol ketal.

The desired compound is prepared by reaction of 4-hydroxy-4-[3-allyloxymethylphenyl]cyclohexan-1-one ethylene glycol ketal, prepared as in step 2, with NaH and iodomethane as described in Example 1, step 2.

Step 4.
4-methoxy-4-(3-allyloxymethylphenyl]cyclohexan-1-one.

The desired compound is prepared by hydrolysis of 4-methoxy-4-[3-allyloxymethylphenyl]cyclohexan-1-one ethylene glycol ketal, prepared as in step 3, using HCl in methanol.

Step 5:
trans-4-methoxy-4-[3-allyloxymethylphenyl]cyclohexan-1-ol.

The desired compound is prepared by reduction of 4-methoxy-4-(3allyloxymethylphenyl)cyclohexan-1-one, prepared as in step 4 using LS-SELECTRIDE (lithium trisiamylborohydride, Aldrich Chemical Co.).

Step 6:
trans-1,4-dimethoxy-4-[3-allyloxymethylphenyl]cyclohexane.

The desired compound is prepared by treatment of trans-4-methoxy-4-[3allyloxymethylphenyl]cyclohexan-1-ol, prepared as in step 3, with NaH and methyl iodide as described in step 3.

Step 71
trans-1,4-dimethoxy-4-[3-hydroxymethylphenyl]cyclohexane.

The desired compound is prepared by removal of the allylloxy protecting group from trans-1,4-dimethoxy-4-[3-allyloxymethylphenyl]cyclohexane, prepared as in step 6, using PdCl₂, aqueous DMF, CuCl, and O₂ according to the method of Mereyala, H. B., and Guntha, S. *Tetrahedron Lett*, 1993, 34(43), 6929.

Step 8: 4-(4-fluorophenyl)-7-[[3-(trans-1,4-dimethoxycyclohexyl)phenyl]methoxy]naptho[2,3-c]furan-1(3H)-one.

The desired compound is prepared by Mitsunobu coupling of trans- 1,4-dimethoxy-4-[3-hydroxymethylphenyl]cyclohexane, prepared as in step 7, and 7-hydroxy-4-(4-fluorophenyl) naptho[2,3-c]furan-1(3H)-one using triphenylphosphine and diisopropylazodicarboxylate (Mitsunobu, O., *Synthesis*, 1981, 1).

The compounds listed in Table 2 are prepared according to the method of Example 25, except substituting the desired 7-hydroxy-4-(aryl)naptho[2,3-c]furan-1(3H)-one, prepared as described in U.S. Pat. No. 5, 227,399, or 7-hydroxy-4(heteroaryl)naptho[2,3-c]furan-1(3H) -one, prepared as described in U.S. Pat. No. 5,252,599 for 7-hydroxy-4-(4-fluorophenyl)naptho[2,3-c]furan-1(3H)-one.

TABLE 2

| Example | Ar |
|---------|-----|
| 26 | phenyl |
| 27 | 4-chlorophenyl |
| 28 | 4-methoxyphenyl |
| 29 | 2-fluorophenyl |
| 30 | 2-chlorophenyl |
| 31 | 3-methoxyphenyl |
| 32 | 2-furyl |
| 33 | 3-furyl |
| 34 | 3-thienyl |
| 35 | 3-pyridyl |

EXAMPLE 36

Preparation of 4-(4-fluorophenyl)-7-[[3-(trans-1,3-dimethoxycyclobutyl)phenyl]methoxy]naptho [2,3-c]furan-1(3H)-one.

Step 1.
cis-3-tert-butyloxy-1-hydroxy-1-[3-allyloxymethylphenyl]cyclobutane.

The desired compound is prepared according to the method of Example 25, step 2, except substituting 3-tert-butyloxycyclobutanone, prepared as described by Potman, R. P., et al., *J. Org. Chem.*, 1984, 49 (19), 3628, for 1,4-cycloheaxanedione mono-ethylene glycol ketal.

Step 2.
cis-3-tert-butyloxy-1-methoxy-1-[3-allyloxymethylphenyl]cyclobutane.

The desired compound is prepared by reaction of 3-tert-butyloxy-1-hydroxy-1-[3-allyloxymethylphenyl]-cyclobutane, prepared as in step 1, with NaH and iodomethane according to the method of Example 1, step 2.

Step 3.
cis-3-hydroxy-1-methoxy-1-[3-allyloxymethylphenyl]-cyclobutane.

The desired compound is prepared according to the method of Example 25, step 4, except substituting cis-3-tert-butyloxy-1-methoxy-1-[3-allyloxymethylphenyl]-cyclobutane, prepared as in step 2, for 4-methoxy-4-[3-allyloxymethylphenyl]cyclohexan-1-one ethylene glycol ketal.

Step 4:
trans-3-benzoyl-1-methoxy-1-(allyloxymethylphenyl)-cyclobutane.

The desired compound is prepared by Mitsunobu coupling of cis-3-hydroxy-1-methoxy-1-[3-allyloxymethylphenyl]cyclobutane, prepared as in step 3, with benzoic acid.

Step 5:
trans-3-hydroxy-1-methoxy-1-(allyloxymethylphenyl)-cyclobutane.

The desired compound is prepared by hydrolysis of trans-3-benzoyl-1-methoxy-1-(allyloxymethylphenyl)-cyclobutane, prepared as in step 4, with aqueous LiOH.

Step 6:
4-(4-fluorophenyl)-7-[[3-(trans-1,3-dimethoxycyclobutyl)phenyl]methoxy]naptho[2,3-c]furan-1-(3H)-one.

The desired compound is prepared according to the method of Example 25, steps 6–8, except substituting trans-3-hydroxy-1-methoxy-1-(allyloxymethylphenyl)-cyclobutane, prepared as in step 5, for trans-1,4-dimethoxy-4-[3-hydroxymethylphenyl]cyclohexane.

The compounds listed in Table 2 are prepared according to the method of Example 25, except substituting the desired 7-hydroxy-4-(aryl)naptho[2,3-c]furan-1(3H)-one, prepared as described in U.S. Pat. No. 5,227,399, or 7-hydroxy-4-(heteroaryl)naptho[2,3-c]furan-1(3H)-one, prepared as described in U.S. Pat. No. 5,252,599 for 7-hydroxy-4-(4-fluorophenyl)naptho[23-c]furan-1(3H)-one.

TABLE 3

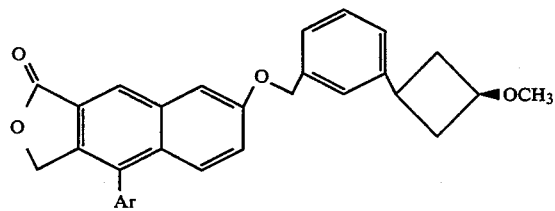

| Example | Ar |
|---------|----|
| 37 | phenyl |
| 38 | 4-chlorophenyl |
| 39 | 4-methoxyphenyl |
| 40 | 2-fluorophenyl |
| 41 | 2-chlorophenyl |
| 42 | 3-methoxyphenyl |
| 43 | 2-furyl |
| 44 | 3-furyl |
| 45 | 3-thienyl |
| 46 | 3-pyridyl |

EXAMPLE 47

Preparation of 3-hydroxymethyl-4-(4-fluorophenyl)-7-[3-(4-methoxytetrahydro-2H-pyran-4-yl)-2-propenyloxy]-2-naphthoic acid, sodium salt.

The desired compound is prepared by heating a mixture in dioxane of 4-(4-fluorophenyl) -7-[(3'-(4''-methoxytetrahydropyran-4''-yl)prop-2'-eneyloxy)]naptho[2,3-c]furan -1(3H)-one, prepared as in Example 1, and aqueous NaOH (1 equiv) for an amount of time sufficient to consume substantially all of the starting material, followed by evaporation to dryness.

EXAMPLE 48

Preparation of 3-hydroxymethyl-4-(4-fluorophenyl)-7-[3-(2-methyl-4-methoxytetrahydro-2H-pyran-4-yl)-2-propenyloxy]-2-naphthoic acid, sodium salt.

The desired compound is prepared by treatment of 4-(4-fluorophenyl)-7-[(3'-(2''-methyl-4''-methoxytetrahydropyran-4''-yl)prop-2'-eneyloxy)]naptho[2,3-c]furan-1(3H)-one, prepared as in Example 4, with NaOH as described in Example 47.

EXAMPLE 49

3-hydroxymethyl-4-(4-fluorophenyl)-7-[[(3-(trans-1,4-dimethoxycyclohexyl)phenyl]methoxy]-2-napthoic acid, sodium salt.

The desired compound is prepared by treatment of 4-(4-fluorophenyl)-7-[[3-(trans-1,4-dimethoxycyclohexyl) phenyl]methoxy]naptho[2,3-c]furan-1(3H)-one, prepared as in Example 25, with NaOH as described in Example 47.

EXAMPLE 50

Preparation of 3-hydroxymethyl-4-(4-fluorophenyl)-7,[[(3-(trans-1,3-dimethoxycyclobutyl)phenyl]methoxy]-2-napthoic acid, sodium salt.

The desired compound is prepared by treatment of 4-(4-fluorophenyl)-7-[[3-(trans-1,3-dimethoxycyclobutyl) phenyl]methoxy]naptho[23-c]furan-1(3H)-one, prepared as in Example 36, with NaOH as described in Example 47.

We claim:

1. A compound or pharmaceutically acceptable salt thereof selected from the group consisting of

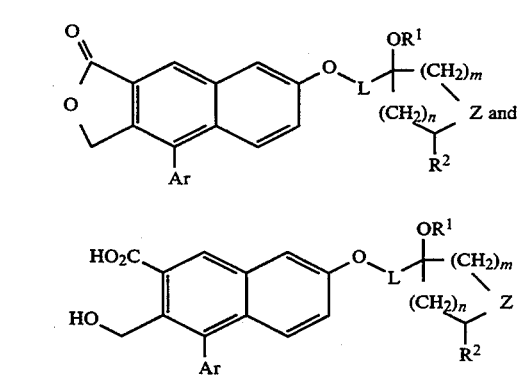

wherein
Ar is selected from the group consisting of
  unsubstituted phenyl,
  phenyl substituted one or more groups selected from
    halogen,
    cyano,
    alkyl of one to four carbon atoms,
    haloalkyl of one to four carbon atoms,
    alkoxy of one to six carbon atoms, and
    alkoxycarbonyl wherein the alkyl portion is of one to four carbon atoms,
  unsubstituted furyl, furyl substituted with one or more groups selected from
halogen,
alkyl of one to four carbon atoms, and
alkoxy of one to four carbon atoms,
unsubstituted pyridyl,
pyridyl substituted with one or more groups selected from
halogen,
alkyl of one to four carbon atoms, and
alkoxy of one to four carbon atoms,
unsubstituted thienyl, and
thienyl substituted with one or more groups selected from
halogen,
alkyl of one to four carbon atoms, and
alkoxy of one to four carbon atoms;
L is selected from the group consisting of
alkylene of one to three carbon atoms,
alkenylene of two to three carbon atoms, and
alkynylene of two to three carbon atoms, and

[structure with (CH₂)ₚ and R⁴ on phenyl ring]

wherein
p is an integer of 1 to 4, inclusive, and R⁴ is selected from the group consisting of
hydrogen,
alkyl of one to four carbon atoms,
halogen
haloalkyl of one to four carbon atoms, and
alkoxy of one to six carbon atoms;
R¹ is selected from the group consisting of
alkyl of one to four carbon atoms,
alkenyl of two to four carbon atoms,
alkynyl of two to four carbon atoms, and
cyclopropylmethyl;
R² is hydrogen or alkyl of one to four carbon atoms;
m is 1 or 2;
Z is oxygen or >CHOR³, wherein R³ is selected from the group consisting of
alkyl of one to four carbon atoms,
alkenyl of two to four carbon atoms,
alkynyl of two to four carbon atoms, and
cyclopropylmethyl; and
n is 0 or 1.

2. A compound or pharmaceutically acceptable salt thereof as defined by claim 1 selected from the group consisting of

[structure with Ar, OR¹, R² groups]

and

-continued

[structure with HO₂C, HO, Ar, OR¹, R² groups]

wherein
L is selected from the group consisting of
alkylene of one to three carbon atoms,
alkenylene of two to three carbon atoms, and
alkynylene of two to three carbon atoms; and
Ar, R¹, and R² are defined therein.

3. A compound as defined by claim 2, or a pharmaceutically acceptable salt thereof wherein Ar is unsubstituted phenyl, or phenyl substituted one or more groups selected from halogen, cyano, alkyl of one to four carbon atoms, haloalkyl of one to four carbon atoms, alkoxy of one to six carbon atoms, and alkoxycarbonyl wherein the alkyl portion is of one to four carbon atoms.

4. A compound or a pharmaceutically acceptable salt thereof as defined by claim 1 selected from the group consisting of
4-(4-fluorophenyl)-7-[3-(4-methoxytetrahydro-2H-pyran-4-yl)-2-propenyloxy]naptho[2,3-c]furan-1(3H)-one,
3-hydroxymethyl-4-(4-fluorophenyl)-7-[3-(4-methoxytetrahydro-2H-pyran -4-yl)-2-propenyloxy]-2-naphthoic acid,
4-(4-methoxyphenyl)-7-[3-(4-methoxytetrahydro-2H-pyran-4-yl)-2-propenyloxy]naptho[2,3-c]furan-1(3H)-one,
3-hydroxymethyl-4-(4-methoxyphenyl)-7-[3-(4-methoxytetrahydro-2H -pyran-4-yl)-2-propenyloxy]-2-naphthoic acid,
4-(2-fluorophenyl)-7-[3-(4-methoxytetrahydro-2H-pyran-4-yl)-2-propenyloxy]naptho[2,3-c]furan-1(3H)-one,
3-hydroxymethyl-4-(2-fluorophenyl)-7-[3-(4-methoxytetrahydro-2H-pyran -4-yl)-2-propenyloxy]-2-naphthoic acid,
4-(fur-2-yl)-7-[3-(4-methoxytetrahydro-2H-pyran-4-yl)-2-propenyloxy]naptho[2,3-c]furan-1(3H)-one,
3-hydroxymethyl-4-(fur-2-yl)-7-[3-(4-methoxytetrahydro-2H-pyran-4-yl)-2-propenyloxy]-2-naphthoic acid,
4-(fur-3-yl)-7-[3-(4-methoxytetrahydro-2H-pyran-4-yl)-2-propenyloxy]naptho[2,3-c]furan-1(3H)-one,
3-hydroxymethyl-4-(fur-3-yl)-7-[3-(4-methoxytetrahydro-2H-pyran-4-yl)-2-propenyloxy]-2-naphthoic acid,
4-(thien-3-yl)-7-[3-(4-methoxytetrahydro-2H-pyran-4-yl)-2-propenyloxy]naptho[2,3-c]furan-1(3H)-one,
3-hydroxymethyl-4-(thien-3-yl)-7-[3-(4-methoxytetrahydro-2H-pyran-4-yl) -2-propenyloxy]-2-naphthoic acid,
4-(4-fluorophenyl)-7-[3-(4-methoxytetrahydro-2H-pyran-4-yl)-2-propynyloxy]naptho[2,3-c]furan-1(3H)-one,
3-hydroxymethyl-4-(4-fluorophenyl)-7-[3-(4-methoxytetrahydro-2H-pyran -4-yl)-2-propynyloxy]-2-naphthoic acid,
4-(4-fluorophenyl)-7-[3-(4-methoxytetrahydro-2H-pyran-4-yl)propyloxy]naptho[2,3-c]furan-1(3H)-one, 3-hydroxymethyl-4-(4-fluorophenyl)-7-[3-(4-methoxytetrahydro-2H-pyran -4-yl)propyloxy]-2-napthoic acid, 4-(4-fluorophenyl)-7-[3-(2-methyl-4-methoxytetrahydro-2H-pyran-4-yl)-2-propenyloxy]naptho[2,3-c]furan-1(3H) -one, 3-hydroxymethyl-4-(4-fluorophenyl)-7-[3-(2-methyl-4-methoxytetrahydro -2H-pyran-4- yl)-2-propenyloxy]-2-napthoic acid, 4-(fur-2-yl)-7-[3-(2-methyl-4-methoxytetrahydro-2H-pyran-4-yl)-2-propenyloxy]naptho[2,3-c]furan-1(3H) -one, 3-hydroxymethyl-4-(fur-2-yl)-7-[3-(2-methyl-4-methoxytetrahydro-2H -pyran-4-yl)-2-propenyloxy]-2-napthoic acid, 4-(fur-3-yl)-7-[3-(2-methyl-4-methoxytetrahydro-2H-pyran-4-yl)-2-propenyloxy]naptho[2,3-c]furan-1(3H)-one, 3-hydroxymethyl-4-(fur-3-yl)-7-[3-(2-methyl-4-methoxytetrahydro-2H -pyran-4-yl)-2-propenyloxy]-2-napthoic acid, 4-(thien-3-yl)-7-[3-(2-methyl-4-methoxytetrahydro-2H-pyran-4-yl)-2-propenyloxy]naptho[2,3-c]furan-1(3H) -one, and 3-hydroxymethyl-4-(thien-3-yl)-7-[3-(2-methyl-4-methoxytetrahydro-2H -pyran-4-yl)-2-propenyloxy]-2-napthoic acid.

5. A compound as defined by claim 1 selected from the group consisting of 4-(4-fluorophenyl)-7-[3-(4-methoxytetrahydro-2H-pyran-4-yl)-2-propenyloxy]naptho[2,3-c]furan-1(3H)-one, and 3-hydroxymethyl-(4-fluorophenyl)-7- [3 -(4-methoxytetrahydro-2H-pyran-4-yl)-2-propenyloxy]-2-napthoic acid, or a pharmaceutically acceptable salt thereof.

6. A compound or pharmaceutically acceptable salt thereof as defined by claim 1 selected from the group consisting of

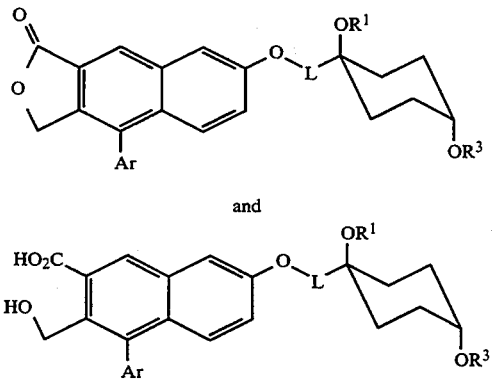

and wherein L is

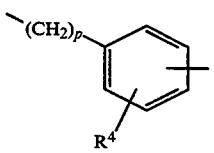

wherein
p is an integer of 1 to 4, inclusive, and $R^4$ is selected from the group consisting of hydrogen,
alkyl of one to four carbon atoms,
halogen,
haloalkyl of one to four carbon atoms, and
alkoxy of one to six carbon atoms;

$R^1$ and $R^3$ are independently selected from the group consisting of
alkyl of one to four carbon atoms,
alkenyl of two to four carbon atoms,
alkynyl of two to four carbon atoms, and
cyclopropylmethyl;

Ar is defined therein.

7. A compound as defined by claim 6, or a pharmaceutically acceptable salt thereof wherein Ar is unsubstituted phenyl, or phenyl substituted one or more groups selected from halogen, cyano, alkyl of one to four carbon atoms, haloalkyl of one to four carbon atoms, alkoxy of one to six carbon atoms, and alkoxycarbonyl wherein the alkyl portion is of one to four carbon atoms.

8. A compound as defined by claim 1 or a pharmaceutically acceptable salt thereof having the formula

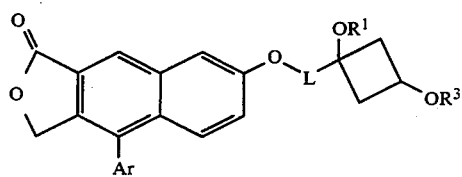

and

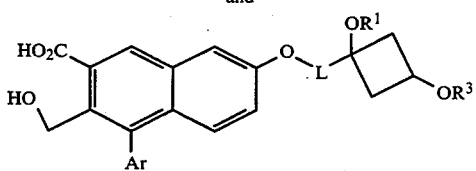

wherein L is

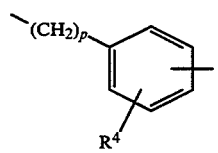

wherein
p is an integer of 1 to 4, inclusive, and $R^4$ is selected from the group consisting of
hydrogen,
alkyl of one to four carbon atoms,
halogen,
haloalkyl of one to four carbon atoms, and
alkoxy of one to six carbon atoms;

$R^1$ and $R^3$ are independently selected from the group consisting of
alkyl of one to four carbon atoms,
alkenyl of two to four carbon atoms,
alkynyl of two to four carbon atoms, and
cyclopropylmethyl;

Ar is defined therein.

9. A compound as defined by claim 8, or a pharmaceutically acceptable salt thereof wherein Ar is unsubstituted phenyl, or phenyl substituted one or more groups selected from halogen, cyano, alkyl of one to four carbon atoms, haloalkyl of one to four carbon atoms, alkoxy of one to six carbon atoms, and alkoxycarbonyl wherein the alkyl portion is of one to four carbon atoms.

10. A pharmaceutical composition for inhibiting the biosynthesis of leukotrienes comprising a therapeutically effective amount of a compound as defined by claim 1 in combination with a pharmaceutically acceptable carrier.

11. A method of inhibiting the biosynthesis of leukotrienes comprising administering to a mammal in need of such treatment a therapeutically effective amount of a compound as defined by claim 1.

* * * * *